United States Patent
Yang et al.

(10) Patent No.: US 10,734,677 B2
(45) Date of Patent: Aug. 4, 2020

(54) SUBSTITUTED IMIDAZOLE AND BENZIMIDAZOLE LITHIUM SALTS

(71) Applicant: Robert Bosch GmbH, Stuttgart (DE)

(72) Inventors: Jin Yang, Pleasanton, CA (US); Hany Basam Eitouni, Oakland, CA (US); Malar Azagarsamy, Fremont, CA (US); Boris Kozinsky, Waban, MA (US); Georgy Samsonidze, Boston, MA (US); Nicola Molinari, Brescia (IT)

(73) Assignee: ROBERT BOSCH GMBH, Stuttgart (DE)

( * ) Notice: Subject to any disclaimer, the term of this patent is extended or adjusted under 35 U.S.C. 154(b) by 105 days.

(21) Appl. No.: 15/698,527

(22) Filed: Sep. 7, 2017

(65) Prior Publication Data
US 2018/0375153 A1    Dec. 27, 2018

Related U.S. Application Data

(63) Continuation-in-part of application No. 15/633,550, filed on Jun. 26, 2017, now abandoned.

(51) Int. Cl.
| | |
|---|---|
| *C07D 233/64* | (2006.01) |
| *H01M 10/0565* | (2010.01) |
| *H01M 10/052* | (2010.01) |
| *H01M 2/14* | (2006.01) |
| *C07F 5/00* | (2006.01) |
| *H01M 4/131* | (2010.01) |

(Continued)

(52) U.S. Cl.
CPC ...... *H01M 10/0565* (2013.01); *C07D 233/64* (2013.01); *C07D 233/90* (2013.01); *C07D 235/10* (2013.01); *C07D 235/18* (2013.01); *C07F 5/00* (2013.01); *C07F 5/022* (2013.01); *H01M 2/14* (2013.01); *H01M 4/131* (2013.01); *H01M 4/364* (2013.01); *H01M 4/602* (2013.01); *H01M 10/052* (2013.01); *H01M 4/505* (2013.01); *H01M 4/525* (2013.01); *H01M 2004/028* (2013.01); *H01M 2300/0025* (2013.01); *H01M 2300/0082* (2013.01)

(58) Field of Classification Search
CPC .. H01M 10/0565; H01M 4/131; H01M 4/364; H01M 4/602; H01M 10/052; C07D 233/64; C07D 235/10; C07F 5/00; C07F 5/022
See application file for complete search history.

(56) References Cited

U.S. PATENT DOCUMENTS

| | | |
|---|---|---|
| 6,534,216 B1 | 3/2003 | Narukawa et al. |
| 7,070,632 B1 | 7/2006 | Visco et al. |

(Continued)

OTHER PUBLICATIONS

International Search Report for PCT/US2017/039322, dated Nov. 13, 2017.

(Continued)

*Primary Examiner* — James Lee
(74) *Attorney, Agent, or Firm* — Brooks Kushman P.C.

(57) ABSTRACT

A new class of electrolyte salts that contain substituted imidazole or benzimidazole groups is described. The salts can be used in non-aqueous electrolytes in lithium or other alkali battery cells. When used with a lithium metal anode, the salts are electrochemically stable up to 5V vs. $Li/Li^+$.

10 Claims, 1 Drawing Sheet

(51) Int. Cl.
*C07D 235/18* (2006.01)
*C07D 235/10* (2006.01)
*C07F 5/02* (2006.01)
*H01M 4/60* (2006.01)
*H01M 4/36* (2006.01)
*C07D 233/90* (2006.01)
*H01M 4/525* (2010.01)
*H01M 4/505* (2010.01)
*H01M 4/02* (2006.01)

(56) References Cited

U.S. PATENT DOCUMENTS

| | | |
|---|---|---|
| 8,927,160 B2 | 1/2015 | Armand et al. |
| 2003/0108800 A1 | 6/2003 | Barbarich |
| 2005/0165214 A1 | 7/2005 | Nobuta et al. |
| 2011/0214895 A1* | 9/2011 | Ihara .................... B25F 5/00 173/217 |
| 2013/0260207 A1 | 10/2013 | Uemura |
| 2014/0178771 A1 | 6/2014 | Chem et al. |
| 2016/0380309 A1 | 12/2016 | Schmidt et al. |

OTHER PUBLICATIONS

International Search Report for PCT/US2018/016052 dated May 30, 2018.
PUBCHEM, Substance Record for SID 315616008, Available Date: Jul. 14, 2016 [retrieved on May 7, 2018]. Retrieved from the Internet:. entire document.
Bitner-Michalska, "Fluorine-free electrolytes for all-solid sodium-ion batteries based on percyano-substituted organic salts," Sci. Rep. 7, 40036; doi: 10.1038/srep40036 (2017).
Polu, "New solid polymer electrolytes (PEO20—LiTDI—Sn) for lithium batteries: structural, thermal and ionic conductivity studies," J Mater Sci: Mater Electron (2015) 26:8548-8554.
Sriana, "Novel benzimidazole salts for lithium ion battery electrolytes: effects of substituents," Phys.Chem.Chem.Phys., 2015, 17, 16462.

* cited by examiner

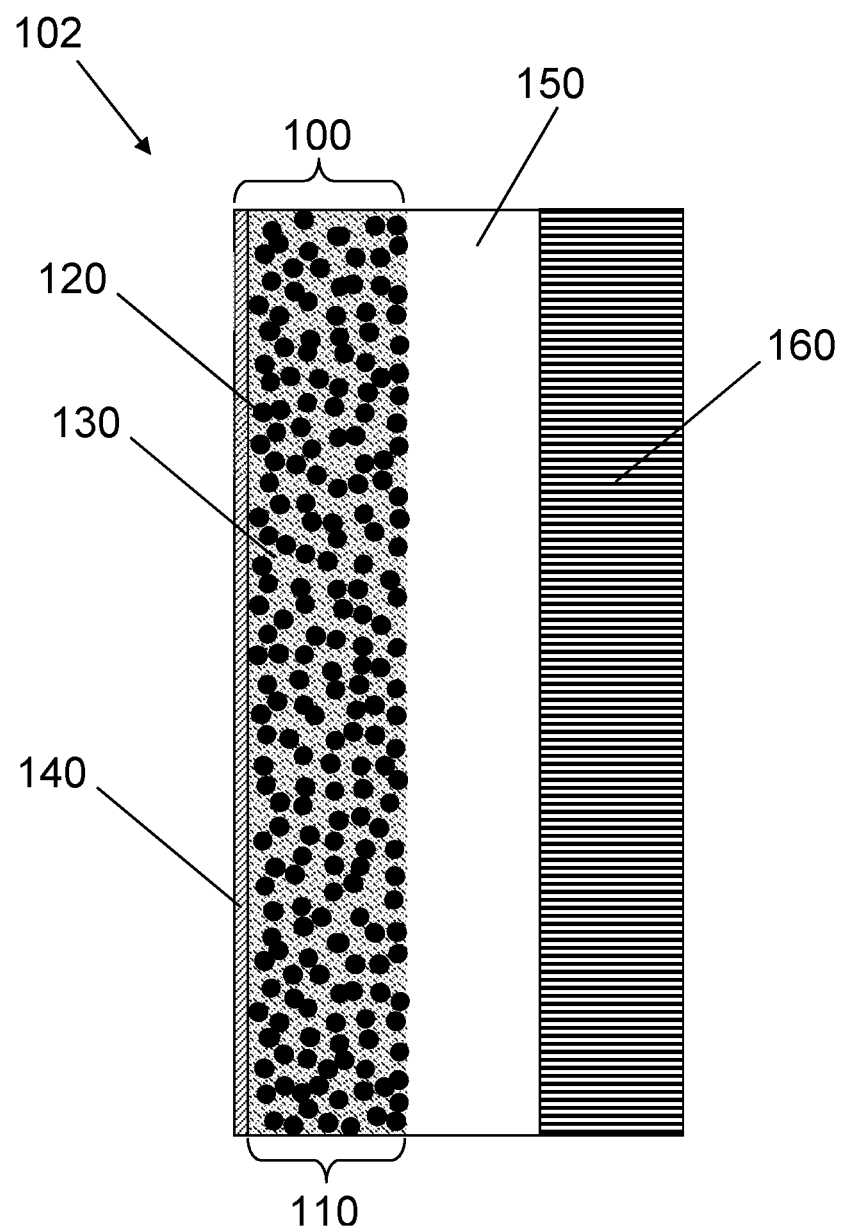

SUBSTITUTED IMIDAZOLE AND BENZIMIDAZOLE LITHIUM SALTS

CROSS-REFERENCE TO RELATED APPLICATIONS

This application is a Continuation-In-Part of U.S. patent application Ser. No. 15/633,550 filed on Jun. 26, 2017, which is incorporated by reference herein.

BACKGROUND OF THE INVENTION

Field of the Invention

This invention relates generally to lithium salts for use in electrolytes in lithium battery cells, and, more specifically, to lithium salts that are stable in high voltage lithium battery cells.

More and more lithium battery manufacturers are using next-generation cathode materials such as NCA (lithium nickel cobalt aluminum oxide), NCM (lithium nickel cobalt manganese oxide), and high energy NCM (HE-NCM—magnesium-rich lithium nickel cobalt manganese oxide) in order to exploit their potentially high gravimetric energy densities (as high as 300-500 Wh/kg), their good rate capabilities and their long-term stability. Cells made with such metal oxide materials often operate at higher voltages (e.g., as high as 4.5V) than do cells (e.g., 3.6-3.8V) with olivine cathode materials such as LFP (lithium iron phosphate). Electrolytes that have been stable at the lower voltages of LFP cells may have difficulty operating at the higher voltages. Such high voltage environments can cause degradation of both the electrolytes and the lithium salts they contain, often due to either their own stability limit or due to reaction with other cell components such as an aluminum current collector. In addition, when a lithium metal anode is used, some lithium salts react with the lithium metal during cycling. Both of these can lead to capacity fade and even cell death.

It is useful in lithium battery cells if a lithium salt has the following properties: high conductivity, good thermal stability, nontoxicity, stability against lithium metal, safety and electrochemical stability at the potential of a fully charged cell (e.g., 4.5V vs. Li/Li$^+$). But few lithium salts have all these properties.

There are inorganic lithium salts and organic lithium salts. Examples of inorganic lithium salts include $LiClO_4$, $LiAsF_6$, $LiPF_6$, and $LiBF_4$. Unfortunately, $LiClO_4$ may explode in use, $LiAsF_6$ is highly toxic, $LiPF_6$ is not stable at high temperatures, and the ion conductivity of $LiBF_4$ is not very high. Examples of organic lithium salts include $LiN(SO_2CF_3)_2$, (LiTFSI), $LiN(SO_2C_2F_5)_2$, (LiBETI), $LiC(SO_2CF_3)_3$, and $LiCF_3SO_3$ (LiTf). However, these lithium salts have the disadvantage of causing corrosion on commonly-used aluminum current collectors in fully charged cells.

LiTFSI, which is commonly used in polymer electrolytes with Li metal anodes, is stable only to less than 4.0V vs. Li/Li$^+$. It would be useful to develop new high conductivity lithium salts that are stable up to higher voltages and that are also stable against Li metal electrodes.

Heterocyclic compounds, such as imidazole or benzimidazole, are useful platforms for designing organic salts. These compounds are interesting due to their large delocalized aromatic rings, which when used to form Li salts enable high ionic disassociation between the ring and the Li ion, leading to high ionic conductivity. Additionally, there are three or more substitutable positions on imidazole and benzimidazole rings, which allow various electronic withdrawing groups or other functional groups to be introduced, providing fine tuning of Li salt properties.

SUMMARY

In various embodiments of the invention, a new class of electrolyte salts that contain substituted imidazole or benzimidazole groups is disclosed. The salts can be used in non-aqueous electrolytes in lithium battery cells. When used with a lithium metal anode, the salts are electrochemically stable up to 5V vs. Li/Li$^+$.

In one embodiment of the invention, a positive electrode is disclosed. The positive electrode includes positive electrode active material particles, optional electronically-conductive particles, and an electrolyte. The electronically-conductive particles may be carbon black. The electrolyte may be any of the electrolytes disclosed herein. In one arrangement, the salts in the electrolytes contain lithium and substituted imidazole or benzimidazole groups. In one arrangement, the positive electrode also includes a binder, and the electrolyte is a liquid. The active material in the positive electrode may be either lithium nickel cobalt aluminum oxide or lithium nickel cobalt manganese oxide.

In another embodiment of the invention, a battery cell is disclosed. The cell contains a positive electrode that contains positive electrode active material particles, optional electronically-conductive particles, and a first electrolyte; a negative electrode that contains either lithium metal or lithium alloy; and a separator region that contains a second electrolyte between the positive electrode and the negative electrode. At least one of the first electrolyte and the second electrolyte is one or more of the electrolytes disclosed herein, and the electrolyte salts contain lithium and substituted imidazole or benzimidazole groups. In one arrangement, the first electrolyte and the second electrolyte are the same. The positive electrode may contain either lithium nickel cobalt aluminum oxide or lithium nickel cobalt manganese oxide. In one arrangement, the positive electrode also includes a binder, and the electrolyte is a liquid.

BRIEF DESCRIPTION OF THE DRAWINGS

The foregoing aspects and others will be readily appreciated by the skilled artisan from the following description of illustrative embodiments when read in conjunction with the accompanying drawings.

FIG. 1 is a schematic illustration of a battery cell, according to an embodiment of the invention.

DETAILED DESCRIPTION

The embodiments of the invention are illustrated in the context of electrolyte salts in high-voltage lithium battery cells. The skilled artisan will readily appreciate, however, that the materials and methods disclosed herein will have application in a number of other contexts where high-voltage stability is desirable.

In this disclosure, the terms "negative electrode" and "anode" are both used to describe a negative electrode. Likewise, the terms "positive electrode" and "cathode" are both used to describe a positive electrode.

It is to be understood that the terms "lithium metal" or "lithium foil," as used herein with respect to negative electrodes, describe both pure lithium metal and lithium-rich metal alloys as are known in the art. Examples of lithium rich metal alloys suitable for use as anodes include Li—Al, Li—Si, Li—Sn, Li—Hg, Li—Zn, Li—Pb, Li—C or any other Li-metal alloy suitable for use in lithium metal batteries. Other negative electrode materials that can be used in the embodiments of the invention include materials in which lithium can intercalate, such as graphite or lithium titanate, and other materials that can absorb and release lithium ions, such as silicon, germanium, tin, and alloys thereof. Many embodiments described herein are directed to batteries with solid polymer electrolytes, which serve the functions of both electrolyte and separator. As it is well known in the art, batteries with liquid electrolytes use an inactive separator material that is distinct from the liquid electrolyte.

In one embodiment of the invention, a metal salt based on benzimidazole has the following structure:

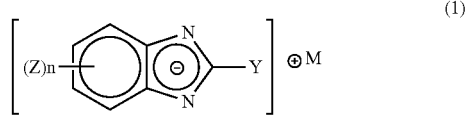
(1)

in which Y may be cyanobenzyl, cyano (—CN), $C_xF_{2x+1}$ (X is an integer that ranges from 0 to 10), or a perfluoropolyether chain; Z may be cyano (—CN), $C_xF_{2x+1}$ (is an integer that ranges from 0 to 10), or perfluoropolyether; and n is an integer that ranges from 1 to 4 and indicates the number of substituents on the aromatic ring. Each of the n Z's is chosen independently from the others, i.e., all the Z's may be different; some may be different and some may be the same; or all may be the same. The metal M may be lithium or some other alkali metal.

In one embodiment of the invention, a metal salt based on benzimidazole has the following structure:

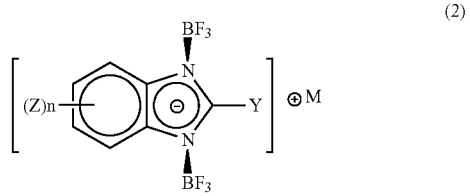
(2)

in which Y may be cyanobenzyl, cyano (—CN), $C_xF_{2x+1}$ (x is an integer that ranges from 0 to 10), or perfluoropolyether; Z may be cyano (—CN), $C_xF_{2x+1}$ (x is an integer that ranges from 0 to 10), or perfluoropolyether; and n is an integer that ranges from 1 to 4 and indicates the number of substituents on the aromatic ring. Each of the n Z's is chosen independently from the others, i.e., all the Z's may be different, some may be different and some may be the same, or all may be the same. The metal M may be lithium or some other alkali metal.

In another embodiment of the invention, a metal salt based on imidazole has the following structure:

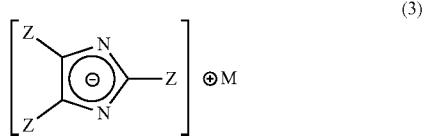
(3)

in which Z may be $C_xF_{2x+1}$ (x is an integer that ranges from 0 to 10) or perfluoropolyether. Each of the Z's is chosen independently from the others, i.e., all the Z's may be different, some may be different and some may be the same, or all may be the same. The metal M may be lithium or some other alkali metal.

A similar metal salt has the following structure:

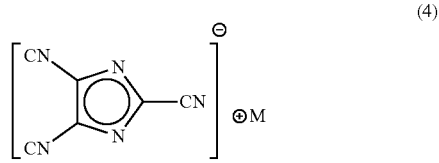
(4)

in which the metal M may be lithium or some other alkali metal.

In another embodiment of the invention, a metal salt based on imidazole has the following structure:

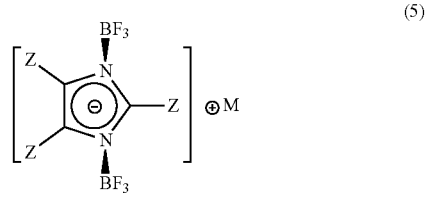
(5)

in which Z may be cyano (—CN), $C_xF_{2x+1}$ (x is an integer that ranges from 0 to 10) or perfluoropolyether. Each of the Z's is chosen independently from the others, i.e., all the Z's may be different, some may be different and some may be the same, or all may be the same. The metal M may be lithium or some other alkali metal.

In another embodiment of the invention, a similar metal salt based on imidazole has the following structure:

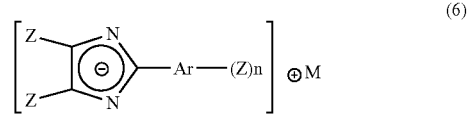
(6)

in which Ar may be an aromatic group, such as phenyl, naphthyl, anthracenyl or a heteroaromatic group, such as pyridinyl, thienyl, imidazolyl, oxazolyl, or indolyl. Z may be cyano (—CN), $C_xF_{2x+1}$ (x is an integer that ranges from 0 to 10), or perfluoropolyether; and n is an integer that ranges from 1 to 9 and indicates the number of substituents on the aromatic ring or rings. Each of the Z's is chosen independently from the others. All the Z's may be different; some may be different and some may be the same; or all may be the same. The metal M may be lithium or some other alkali metal.

In another embodiment of the invention, a similar metal salt based on benzimidazole has the following structure:

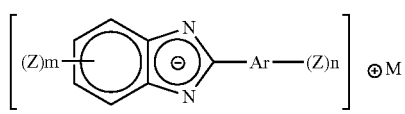
(7)

in which Ar may be an aromatic group, such as phenyl, naphthyl, anthracenyl or a heteroaromatic group, such as pyridinyl, thienyl, imidazolyl, oxazolyl, or indolyl. Z may be cyano (—CN), $C_xF_{2x+1}$ (x is an integer that ranges from 0 to 10), or a perfluoropolyether; m is an integer that ranges from 1 to 4 and indicates the number of substituents on the aromatic ring; and n is an integer that ranges from 1 to 9 and indicates the number of substituents on the aromatic ring or rings. Each of the m Z's is chosen independently from the others. Each of the n Z's is chosen independently from the others. Each one of the m and n Z's may be different, some may be different and some may be the same, or all may be the same. The metal M may be lithium or some other alkali metal.

In another embodiment of the invention, a metal salt based on imidazole has the following structure:

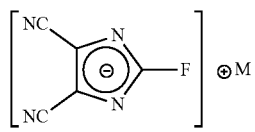
(8)

in which the metal M may be lithium or some other alkali metal.

In another embodiment of the invention, a metal salt based on imidazole has the following structure:

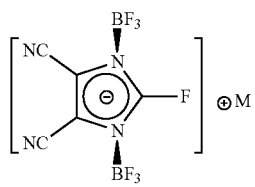
(9)

in which the metal M may be lithium or some other alkali metal.

The salts disclosed herein have good stability against a Li metal anode and have electrochemical stability up to 5V vs. Li/Li$^+$.

Quantum chemistry calculations were performed to determine the relative ionization potential of various salts disclosed herein. Ionization potential is related to oxidation stability: the higher the ionization potential, the greater the oxidation stability. The molecular structures of the salt anions were optimized in vacuum using the PBE0 hybrid density-functional and the aug-cc-pVTZ basis set. The energies of different charge states were computed using the M06-HF hybrid density-functional and the aug-cc-pVTZ basis set. The absolute ionization potentials were obtained as the total energy differences between the neutral and anion states. The relative ionization potentials were obtained by subtracting 1.4 eV (the absolute reduction potential for Li/Li$^+$) from the absolute ones. The results of the calculations are shown in Table I below.

TABLE I

Relative Ionization Potentials for Various Salts (from computer calculations)

| Salt Structure | Relative Ionization Potential vs Li/Li+ (eV) |
|---|---|
| [benzimidazole with F3C substituents, BF3⁻ groups] | 6.30 |
| [benzimidazole with CF3 substituents, BF3⁻ groups] | 5.82 |
| [imidazole with CF3 substituents] | 4.33 |
| [imidazole with NC and CN substituents, phenyl] | 3.93 |
| [imidazole with CF3 substituents and BF3⁻ groups] | 6.60 |
| [imidazole with NC, CN substituents and BF3⁻ groups] | 6.53 |
| [imidazole with NC and CN substituents] | 4.54 |
| [benzimidazole with NC and CN substituents, phenyl] | 3.56 |

The ionization potentials from quantum chemistry calculations can be used to predict the voltage stabilities of the salts in an electrochemical device. The values listed in Table I are the predicted voltage stabilities for the salt structures shown. Based on these values, some salts are predicted to be stable to voltages greater than 4.5 V vs Li/Li$^+$, while some are predicted to be stable to voltages greater than 5V vs Li/Li$^+$. Bitner-Michalska. et al. (*Sci. Rep.* 7, 40036; doi: 10.1038/srep40036 (2017)) have reported sodium salt (sodium 2,4,5-tricyanoimidazolate), which is shown as (4) above, to be stable to approximately 4.2V vs Na/Na+ as determined experimentally. This is in good agreement with the calculated value of 4.5V vs Li/Li+ which was obtained from calculations and is shown in Table I above.

Electrolytes

In one embodiment of the invention, the salts disclosed herein are used with any polymer, such as a solid polymer, that is appropriate for use in a Li battery. Examples of polymers that can be used with the salts disclosed herein to form a solid polymer electrolyte include, but are not limited to, homopolymers, random copolymers, graft copolymers, and block copolymers that contain ionically-conductive blocks and structural blocks that make up ionically-conductive phases and structural phases, respectively. The ionically-conductive polymers or phases may contain one or more linear or non-linear polymers such as polyethers, polyesters, polyamines, polyimides, polyamides, poly alkyl carbonates, polynitriles, perfluoro polyethers, polysiloxanes, polyalkoxysiloxanes, polyphosphazines, polyolefins, polydienes, and fluorocarbon polymers substituted with high dielectric constant groups such as nitriles, carbonates, and sulfones, and combinations thereof. The linear polymers can also be used in combination as graft copolymers with polysiloxanes, polyalkoxysiloxanes, polyphosphazines, polyolefins, and/or polydienes to form the conductive phase. The structural phase may be made of polymers such as polystyrene, hydrogenated polystyrene, polymethacrylate, poly(methyl methacrylate), polyvinylpyridine, polyvinylcyclohexane, polyimide, polyamide, polypropylene, polyolefins, poly(t-butyl vinyl ether), poly(cyclohexyl methacrylate), poly(cyclohexyl vinyl ether), poly(t-butyl vinyl ether), polyethylene, poly(phenylene oxide), poly(2,6-dimethyl-1, 4-phenylene oxide) (PXE), poly(phenylene sulfide), poly(phenylene sulfide sulfone), poly(phenylene sulfide ketone), poly(phenylene sulfide amide), polysulfone, fluorocarbons, such as polyvinylidene fluoride, or copolymers that contain styrene, methacrylate, or vinylpyridine. It is especially useful if the structural phase is rigid and is in a glassy or crystalline state. In various arrangements, the polymer electrolyte has a molecular weight greater than 250 Da, greater than 1,000 Da, greater than 5,000 Da, greater than 10,000 Da, greater than 20,000 Da, greater than 100,000 Da, or any range subsumed therein.

In one embodiment of the invention, the salts disclosed herein are used in any organic liquid that is appropriate for use in a Li battery. Examples of organic liquids that can be used with the salts disclosed herein to form a liquid electrolyte include, but are not limited to, polyethylene glycol dimethyl ether (PEGDME), diethyl carbonate (DEC), ethylene carbonate (EC), propylene carbonate (PC), dimethylformamide (DMF), dimethylcarbonate, acetonitrile, succinonitrile, glutaronitrile, adiponitrile and combinations thereof. Other examples of liquid electrolytes are ionic liquids, including but not limited to, alkyl substituted pyridinium-based ionic liquids with bis(trifluoromethane)sulfonamide (TFSI), fluoralkylphosphate (FAP), tetracyanoborate (TCB), bis(oxalato)borate (BOB), PF6, or BF4 anions; alkyl substituted pyrrolidinium-based ionic liquids with TFSI, FAP, TCB, BOB, PF6, or BF4 anions; alkyl substituted ammonium-based ionic liquids with TFSI, FAP, TCB, BOB, PF6, or BF4 anions; alkyl substituted piperidinium-based ionic liquids with TFSI, FAP, TCB, BOB, PF6, or BF4 anions, and combinations thereof. In general, liquid electrolytes may be used in combination to form electrolyte mixtures. As is well known in the art, batteries with organic liquid electrolytes may be used with an inactive separator membrane that is distinct from the organic liquid electrolyte.

In one embodiment of the invention, the salts disclosed herein are used in any ionically-conductive gel that is appropriate for use in a Li battery. Examples of gels that can be used with the salts disclosed herein to form a gel electrolyte include, but are not limited to, polymers such as polyethylene oxide (PEO), polyacrylonitrile (PAN), poly(methyl methacrylate) (PMMA), poly(vinylidene fluoride) (PVDF), poly(vinyl pyrrolidinone) (PVP), poly(vinyl acetate) (PVAC), poly(vinylidene fluoride)-co-hexafluoropropylene (PVDF-HFP), and combinations thereof mixed with a liquid electrolyte such as those listed above.

Positive Electrode Materials

The positive electrode active material can be any of a variety of materials depending on the type of chemistry for which the cell is designed. In one embodiment of the invention, the cell is a lithium or lithium ion cell. The positive electrode active material can be any material that can serve as a host material for lithium ions. Examples of such materials include, but are not limited to materials described by the general formula $Li_xA_{1-y}M_yO_2$, wherein A comprises at least one transition metal selected from the group consisting of Mn, Co, and Ni; M comprises at least one element selected from the group consisting of B, Mg, Ca, Sr, Ba, Ti, V, Cr, Mn, Fe, Co, Ni, Cu, Al, In, Nb, Mo, W, Y, and Rh; x is described by $0.05 \leq x \leq 1.1$; and y is described by $0 \leq y \leq 0.5$. In one arrangement, the positive electrode material is $LiNi_{0.5}Mn_{0.5}O_2$.

In one arrangement, the positive electrode active material is described by the general formula: $Li_xMn_{2-y}M_yO_2$, where M is chosen from Mn, Ni, Co, and/or Cr; x is described by $0.05 \leq x \leq 1.1$; and y is described by $0 \leq y \leq 2$. In another arrangement, the positive electrode active material is described by the general formula: $Li_xM_yMn_{4-y}O_8$, where M is chosen from Fe and/or Co; x is described by $0.05 \leq x \leq 2$; and y is described by $0 \leq y \leq 4$. In another arrangement, the positive electrode active material is given by the general formula $Li_x(Fe_yM_{1-y})PO_4$, where M is chosen from transition metals such as Mn, Co and/or Ni; x is described by $0.9 \leq x \leq 1.1$; and y is described by $0 \leq y \leq 1$. In yet another arrangement, the positive electrode active material is given by the general formula: $Li(Ni_{0.5-x}Co_{0.5-x}M_{2x})O_2$, where M is chosen from Al, Mg, Mn, and/or Ti; and x is described by $0 \leq x \leq 0.2$. In some arrangements, the positive electrode material includes $LiNiVO_2$.

Examples of appropriate positive electrode active materials also include compounds such as, $FeS_2$, FeOF, $FeF_3$, $FeF_2$, $MoO_3$, sulfur, lithium polysulfides, CuO, $Cu_2O$, FeO, $Fe_2O_3$, $V_6O_{13}$, $VO_2$, $Li_{1+x}V_3O_8$ ($0 \leq x \leq 3$), $Ag_xV_2O_5$ ($0 < x \leq 2$), $Cu_xV_4O_{11}$ ($0 \leq x \leq 3$), $VOPO_4$, $LiCoO_2$, lithium iron phosphate (LFP), lithium nickel cobalt manganese oxide (NCM), lithium nickel cobalt aluminum oxide (NCA), or mixtures thereof.

The salts disclosed herein are especially useful with positive electrode active materials that operate at high voltages (e.g., as high as 4.5V), such as NCA (lithium nickel cobalt aluminum oxide), NCM (lithium nickel cobalt manganese oxide), and high voltage spinel $LiNi_xMn_{2-x}O_4$ ($0 \leq x \leq 2$).

Negative Electrode Materials

The negative electrode active material can be any of a variety of materials depending on the type of chemistry for which the cell is designed. In one embodiment of the invention, the cell is a lithium or lithium ion cell. The negative electrode material can be any material that can serve as a host material (i.e., can absorb and release) for lithium ions. Examples of such materials include, but are not limited to graphite, lithium titanate, lithium metal, and lithium alloys such as Li—Al, Li—Si, Li—Sn, and Li—Mg. Silicon and silicon alloys are known to be useful as negative electrode materials in lithium cells. Examples include silicon alloys of tin (Sn), nickel (Ni), copper (Cu), iron (Fe), cobalt (Co), manganese (Mn), zinc (Zn), indium (In), silver (Ag), titanium (Ti), germanium (Ge), bismuth (Bi), antimony (Sb), and chromium (Cr) and mixtures thereof. In some arrangements, metal oxides, silicon oxides or silicon carbides can also be used as negative electrode materials.

Battery Cells

FIG. 1 is a cross-sectional schematic drawing of an electrochemical cell 102, according to an embodiment of the invention. It has a positive electrode assembly 100 that includes a positive electrode film 110 and a current collector 140. The positive electrode film 110 has positive electrode active material particles 120, which may be embedded in a matrix of solid electrolyte 130 that also contains small, electronically-conductive particles (as indicated by small grey dots) such as carbon black. The solid polymer electrolyte 130 can be a polymer, a copolymer, or a blend thereof. In one arrangement, the solid polymer electrolyte 130 is a block copolymer electrolyte. In another arrangement (not shown), the positive electrode film 110 has positive electrode active material particles 120 that are held together by a binder such as PVDF, and liquid or gel electrolyte fills the spaces between the positive electrode active material particles 120. There is a positive electrode current collector 140 that may be a continuous or reticulated metal film as described above. There is a negative electrode 160 that is a metal layer, such as a lithium metal or lithium alloy layer, which acts as both negative electrode active material and negative electrode current collector. In one arrangement, similar to the positive electrode assembly, the negative electrode (not shown) has a negative electrode film and a current collector. The negative electrode film contains negative electrode active material particles (e.g., graphite or silicon-containing particles) that may be embedded in a matrix of solid polymer electrolyte that may also contains small, electronically-conductive particles such as carbon black. The solid polymer electrolyte in the negative electrode may or may not be the same as the solid polymer electrolyte 130 in the positive assembly 100. In another arrangement (not shown), the negative electrode 160 has negative electrode active material particles 120 that are held together by a binder such as PVDF, and liquid or gel electrolyte fills the spaces between the negative electrode active material particles. There is a separator region 150 filled with an electrolyte that provides ionic communication between the positive electrode film 110 and the negative electrode 160. In one arrangement, the separator region 150 contains a solid electrolyte and can be the same solid electrolyte (without the carbon particles) as is used in the positive electrode film 110 and/or in the negative electrode assembly.

EXAMPLES

The following examples provide details relating to synthesis of salts in accordance with the present invention. It should be understood the following are representative only, and that the invention is not limited by the detail set forth in these examples.

Example 1—Synthesis of (1)

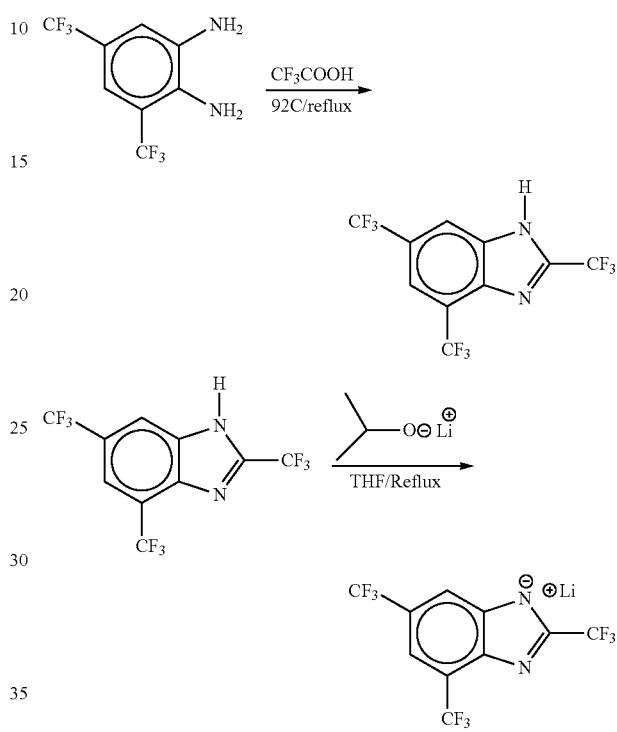

Example 2—Synthesis of (2)

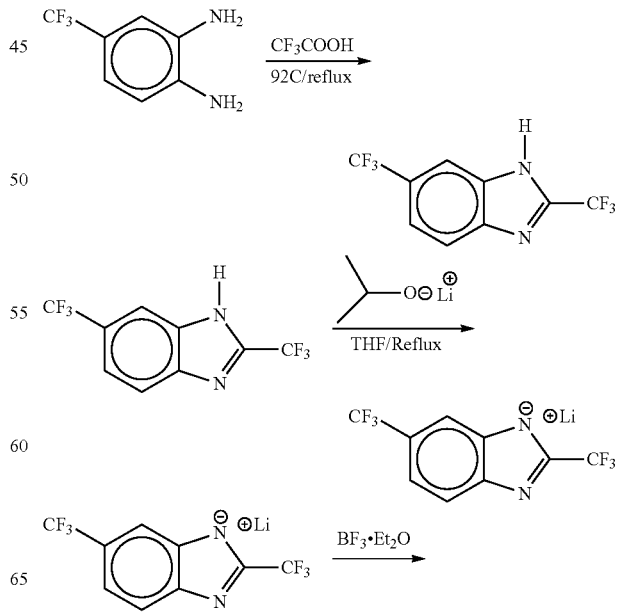

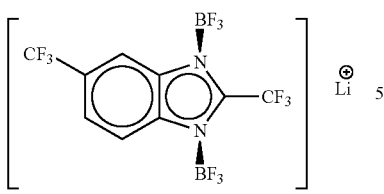

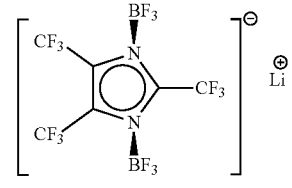

Example 3—Synthesis of (3)

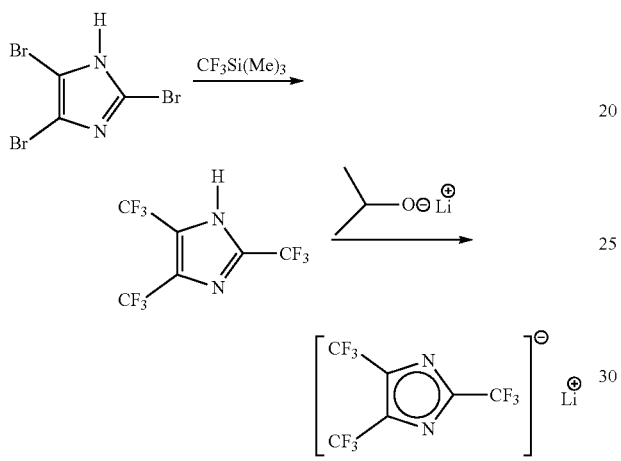

Example 4—Synthesis of (4)

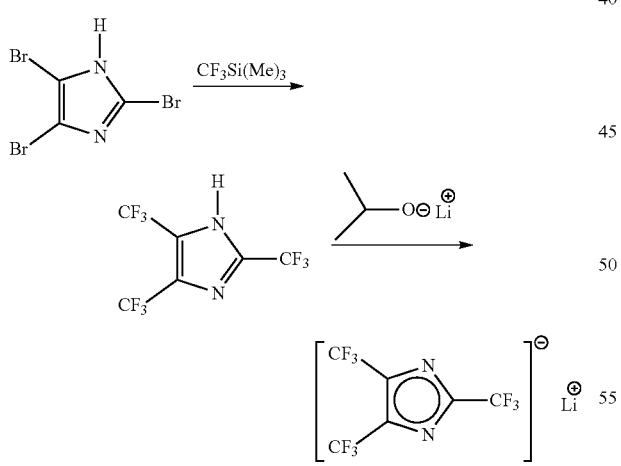

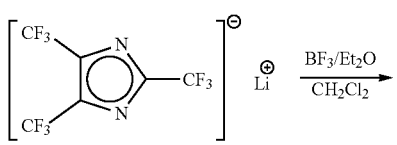

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

We claim:

1. A composition comprising:

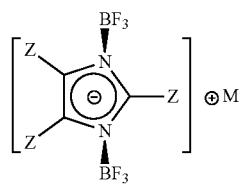

wherein each Z is selected independently from the group consisting of cyano, perfluoropolyether, and $C_xF_{2x+1}$ groups, wherein x is an integer that ranges from 0 to 10 and wherein at least one Z is a perfluoropolyether; and M is an alkali metal.

2. The composition of claim 1 further comprising:
a material selected from the group consisting of one or more of polyethers, polyesters, polyalkoxysiloxanes, polyamines, polyimides, polyamides, poly alkyl carbonates, polynitriles, perfluoro polyethers, fluorocarbon polymers substituted with nitriles, fluorocarbon polymers substituted with carbonates, fluorocarbon polymers substituted with sulfones, polysiloxanes, polyphosphazines, polyolefins, polydienes, and alkyl carbonates;
wherein the composition is an electrolyte.

3. A positive electrode, comprising:
positive electrode active material particles;
electronically-conductive particles; and
a matrix of a solid electrolyte material embedding the positive electrode active material particles and the electronically-conductive particles;
wherein the solid electrolyte material has a composition:

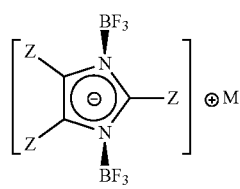

wherein each Z is selected independently from the group consisting of cyano, perfluoropolyether, and $C_xF_{2x+1}$ groups, wherein x is an integer that ranges from 0 to 10 and wherein at least one Z is a perfluoropolyether; and wherein M is an alkali metal.

4. The positive electrode of claim 3 wherein the solid electrolyte material comprises lithium.

5. The positive electrode of claim 3 wherein the positive electrode further comprises a binder.

6. The positive electrode of claim 3 wherein the positive electrode comprises either lithium nickel cobalt aluminum oxide or lithium nickel cobalt manganese oxide, and the solid electrolyte material comprises lithium.

7. A battery cell, comprising:
a positive electrode comprising positive electrode active material particles, electronically-conductive particles, and a matrix of a first solid electrolyte embedding the positive electrode active material particles and the electronically-conductive particles;
a negative electrode comprising lithium metal or lithium alloy; and
a separator region between the positive electrode and the negative electrode, the separator region comprising a second electrolyte, the second electrolyte providing ionic communication between the positive electrode and the negative electrode;
wherein at least one of the first solid electrolyte and the second electrolyte has a composition:

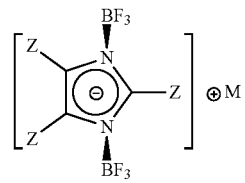

wherein each Z is selected independently from the group consisting of cyano, perfluoropolyether, and $C_xF_{2x+1}$ groups, wherein x is an integer that ranges from 0 to 10 and wherein at least one Z is a perfluoropolyether; and wherein M is an alkali metal.

8. The battery cell of claim 7 wherein the positive electrode comprises either lithium nickel cobalt aluminum oxide or lithium nickel cobalt manganese oxide, and the alkali metal is lithium.

9. The battery cell of claim 7 wherein the first solid electrolyte and the second electrolyte are the same.

10. The battery cell of claim 7 wherein the positive electrode further comprises a binder.

* * * * *